US010799087B2

(12) United States Patent
Miyai

(10) Patent No.: US 10,799,087 B2
(45) Date of Patent: Oct. 13, 2020

(54) ENDOSCOPE SYSTEM, OPERATION METHOD FOR ENDOSCOPE SYSTEM, AND PROGRAM FOR BALANCING CONFLICTING EFFECTS IN ENDOSCOPIC IMAGING

(71) Applicant: SONY CORPORATION, Tokyo (JP)

(72) Inventor: Takeshi Miyai, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 339 days.

(21) Appl. No.: 15/985,322

(22) Filed: May 21, 2018

(65) Prior Publication Data
US 2018/0263462 A1 Sep. 20, 2018

Related U.S. Application Data

(63) Continuation of application No. 15/112,234, filed as application No. PCT/JP2015/081823 on Nov. 12, 2015, now Pat. No. 9,986,890.

(30) Foreign Application Priority Data

Nov. 25, 2014 (JP) .................................. 2014-237702

(51) Int. Cl.
*A61B 1/04* (2006.01)
*H04N 5/217* (2011.01)
(Continued)

(52) U.S. Cl.
CPC ...... *A61B 1/00009* (2013.01); *A61B 1/00016* (2013.01); *A61B 1/00045* (2013.01);
(Continued)

(58) Field of Classification Search
CPC .... A61B 1/00009; A61B 1/04; H04N 5/2256; H04N 5/23229; H04N 5/235; H04N 5/217;
(Continued)

(56) References Cited

U.S. PATENT DOCUMENTS 4,888,639 A 12/1989 Yabe
2007/0009170 A1 1/2007 Lin
(Continued)

FOREIGN PATENT DOCUMENTS

CN 102754443 A 10/2012
JP 01-185240 7/1989
(Continued)

OTHER PUBLICATIONS

Office Action issued in Japanese Application 2016-193685 dated Sep. 3, 2019.
(Continued)

Primary Examiner — John P Leubecker
(74) Attorney, Agent, or Firm — Xsensus LLP

(57) ABSTRACT

The present technology relates to an endoscope system in which resolution and an S/N ratio are adjusted to be well-balanced depending on an imaging condition, and further capable of changing a processing load depending on the imaging condition, a method for operating the endoscope system, and a program.
From an image signal in a body cavity imaged by an endoscope apparatus, a low frequency image including a low frequency component and a high frequency image including a high frequency component are extracted. The low frequency image is reduced by a predetermined reduction ratio, and, after image quality improvement processing is performed, is enlarged by an enlargement ratio corresponding to the reduction ratio. At that time, based on condition information indicating an imaging state, when brightness at the time of imaging is sufficient and the high frequency component does not include noise components a lot, the low frequency image and the high frequency image are added to be output as an output image. In addition, based on the condition information, when the brightness at the time
(Continued)

of imaging is not sufficient and the high frequency component includes the noise components a lot, only the low frequency image is output as the output image. The present technology can be applied to the endoscope system.

15 Claims, 11 Drawing Sheets

(51) Int. Cl.
    *H04N 5/357* (2011.01)
    *A61B 1/00* (2006.01)
    *G02B 23/24* (2006.01)
    *G06T 5/00* (2006.01)
    *G06T 7/00* (2017.01)
    *H04N 9/04* (2006.01)
    *A61B 1/06* (2006.01)
    *A61B 1/313* (2006.01)
    *G06T 5/50* (2006.01)
    *H04N 5/232* (2006.01)
    *H04N 5/225* (2006.01)
(52) U.S. Cl.
    CPC ............ *A61B 1/00096* (2013.01); *A61B 1/04* (2013.01); *A61B 1/043* (2013.01); *A61B 1/0661* (2013.01); *A61B 1/3132* (2013.01); *G02B 23/2484* (2013.01); *G06T 5/002* (2013.01); *G06T 5/003* (2013.01); *G06T 5/50* (2013.01); *G06T 7/0012* (2013.01); *H04N 5/217* (2013.01); *H04N 5/23229* (2013.01); *H04N 9/045* (2013.01); *A61B 1/0005* (2013.01); *A61B 1/0638* (2013.01); *G06T 2207/10024* (2013.01); *G06T 2207/10048* (2013.01); *G06T 2207/10068* (2013.01); *G06T 2207/20016* (2013.01); *G06T 2207/20021* (2013.01); *G06T 2207/20182* (2013.01); *G06T 2207/20216* (2013.01); *G06T 2207/20221* (2013.01); *G06T 2207/30032* (2013.01); *G06T 2207/30096* (2013.01); *H04N 5/357* (2013.01); *H04N 2005/2255* (2013.01)
(58) Field of Classification Search
    CPC . H04N 5/911; H04N 5/357; H04N 2005/2255
    USPC ........................................................ 600/109
    See application file for complete search history.

(56) References Cited

U.S. PATENT DOCUMENTS

| | | |
|---|---|---|
| 2008/0122953 A1 | 5/2008 | Wakahara |
| 2008/0180749 A1 | 7/2008 | Pollard |
| 2009/0092337 A1 | 4/2009 | Nagumo |
| 2010/0026856 A1 | 2/2010 | Jang |
| 2010/0128147 A1 | 5/2010 | Chang |
| 2010/0182452 A1 | 7/2010 | Utsugi |
| 2010/0225782 A1 | 9/2010 | Sambongi |
| 2011/0052095 A1 | 3/2011 | Deever |
| 2011/0096201 A1 | 4/2011 | Yoo |
| 2011/0109754 A1 | 5/2011 | Matsunaga |
| 2011/0150411 A1* | 6/2011 | Sugiyama ............ H04N 19/647 386/224 |
| 2011/0199542 A1 | 8/2011 | Hirai |
| 2011/0200270 A1* | 8/2011 | Kameyama ............... G06T 1/00 382/260 |
| 2011/0249135 A1 | 10/2011 | Minato |
| 2012/0220824 A1 | 8/2012 | Kaku |
| 2012/0327205 A1 | 12/2012 | Takahashi |
| 2013/0063623 A1 | 3/2013 | Kawaguchi |
| 2013/0071025 A1 | 3/2013 | Jang |
| 2013/0342736 A1 | 12/2013 | Numata |
| 2014/0022419 A1 | 1/2014 | Hirai |
| 2014/0044375 A1 | 2/2014 | Xu et al. |
| 2014/0210973 A1 | 7/2014 | Takahashi |
| 2014/0240555 A1 | 8/2014 | Fainstain |
| 2014/0347557 A1* | 11/2014 | Gomita ................... G06T 3/403 348/441 |

FOREIGN PATENT DOCUMENTS

| | | |
|---|---|---|
| JP | 2000-148987 A | 5/2000 |
| JP | 2007-300972 A | 11/2007 |
| JP | 2009-100936 | 5/2009 |
| JP | 2009-253760 A | 10/2009 |
| JP | 2011-135983 | 7/2011 |
| JP | 2011-193983 | 10/2011 |
| JP | 2011-218090 | 11/2011 |
| JP | 2012-75545 A | 4/2012 |
| JP | 2014-002635 A | 1/2014 |
| WO | 2011/099138 A1 | 8/2011 |

OTHER PUBLICATIONS

Office Action for JP Patent Application No. 2016-537591, dated Jul. 14, 2016, 4 pages.

Written Opinion of the International Searching Authority received for PCT Patent Application No. PCT/JP2015/081823, dated Feb. 9, 2016, 6 pages of Written Opinion including 3 pages of English translation.

Combined Chinese Office Action and Search Report dated Jul. 24, 2018 in Patent Application No. 2015800048554 (with English language translation) citing document AO therein, 15 pages.

Office Action dated Mar. 19, 2020 in Japanese Patent Application No. 2016-193685, 8 pages.

\* cited by examiner

--Background Art--

ENDOSCOPE SYSTEM, OPERATION METHOD FOR ENDOSCOPE SYSTEM, AND PROGRAM FOR BALANCING CONFLICTING EFFECTS IN ENDOSCOPIC IMAGING

CROSS-REFERENCE TO RELATED APPLICATIONS

The present application is a continuation of U.S. application Ser. No. 15/112,234, filed on Jul. 8, 2016, now U.S. Pat. No. 9,986,890, which is a U.S. National Stage Entry of PCT Application No. PCT/JP2015/081823, filed on Nov. 12, 2015, and claims priority to Japanese Patent Application 2014-237702, filed on Nov. 25, 2014, the entire contents of each of which is incorporated herein by reference.

TECHNICAL FIELD

The present technology relates to an endoscope system, a method for operating the endoscope system, and a program, and, in particular, relates to an endoscope system in which reduction of a processing load and improvement of resolution can be adjusted to be well-balanced depending on imaging condition in image quality improvement processing of an image imaged by an endoscope apparatus configuring the endoscope system, a method for operating the endoscope system, and a program.

BACKGROUND ART

Imaging with an endoscope system includes imaging utilizing special light such as narrow band light and near infrared light for infrared radiation (IR) observation and photodynamic diagnosis (PDD) observation, in addition to general white light.

For an imaging technology using such special light, for example, a technology has been devised using an input image imaged by using the special light with processing using frequency separation (see Patent Document 1).

CITATION LIST

Patent Document

Patent Document 1: Japanese Patent Application Laid-Open No. 2012-075545

SUMMARY OF THE INVENTION

Problems to be Solved by the Invention

By the way, in the endoscope system and the like, when all image processing is performed in the size as it is of the input image imaged, a configuration capable of processing in real time is necessary, so that processing cost (processing time, scale of hardware for performing processing) is increased. In particular, due to the fact that resolution has been increased in image size that is imaged in recent years, such as High Definition (HD) and 4K (horizontal 4000× vertical 2000 roughly), that tendency is remarkable.

As described above, the imaging in the endoscope system includes normal imaging using white light as illumination light, and special light imaging using special light such as narrow band light and near infrared light. Although property is different in input signals since those are different in an amount of light, the image processing is the same even when any of the illumination light is used, so that it may not necessarily have been suitable for a characteristic of each image signal and waste of processing may have been generated.

The present technology has been made in view of such circumstances, and, in particular, allows to adjust to be well-balanced conflicting effects such as reduction of a processing load according to the image processing and image quality improvement, depending on the imaging condition according to brightness such as a type of illumination light and a lens aperture.

Solutions to Problems

An endoscope system of an aspect of the present technology includes: an endoscope provided with an objective lens at a tip of an insertion portion to be inserted into a body cavity; an image capturing unit that captures an optical image input from the endoscope and condensed by the objective lens, and that outputs the captured image as an image signal; a low-frequency component extracting unit that extracts a low-frequency image with a frequency component lower than the image signal; a high-frequency component extracting unit that extracts a high-frequency image with a frequency component higher than the image signal; an image quality enhancement processor that applies image quality enhancement processing to the low-frequency image; and an output unit that at least outputs the low-frequency image, whose image quality has been enhanced by the image quality enhancement processor, as an output image, and the output unit can be made to output, as the output image, an image signal including pixel values obtained by adding pixel values of individual pixels of the high-frequency image to pixel values of individual pixels of the low-frequency image, whose image quality has been enhanced, in accordance with condition information upon image capturing performed by the image capturing unit.

The condition information can be information indicating whether a condition is satisfied, under which the image signal captured by the image capturing unit has a higher proportion of a noise component.

The information, out of the condition information, indicating whether a condition is satisfied, under which the image signal captured by the image capturing unit can be made to have a higher proportion of a noise component, includes information indicating a type of light emitted by a light source device that emits illuminating light when the image capturing unit captures an image, and information on an aperture of the objective lens in the endoscopic device and an aperture of a relay lens located between the image capturing unit and the objective lens.

The endoscope system can be made to further include a size-reduction unit that reduces a size of the low-frequency image at a certain reduction ratio; and an enlargement unit that enlarges an image at an enlargement ratio corresponding to the reduction ratio, and the image quality enhancement processor can be made to apply image quality enhancement processing to the size-reduced low-frequency image.

The size-reduction unit can be made to reduce the size of the low-frequency image at a reduction ratio in accordance with the condition information, and the enlargement unit can be made to enlarge the size-reduced low-frequency image, having been subjected to image quality enhancement processing, at an enlargement ratio corresponding to the reduction ratio in accordance with the condition information.

The image quality enhancement processor can be made to include processing of spatial-directional noise reduction, time-directional noise reduction, color correction, and frequency band emphasis.

The high-frequency component extracting unit can be made to stop extracting the high-frequency image from the image signal when a condition is satisfied, under which the image signal captured by the image capturing unit has a higher proportion of a noise component, in accordance with condition information upon image capturing performed by the image capturing unit.

A method for operating an endoscope system of an aspect of the present technology:
captures an optical image input from an endoscope provided with an objective lens at a tip of an insertion portion to be inserted into a body cavity, the optical image being condensed by the objective lens, and outputting the captured image as an image signal; extracts a low-frequency image with a frequency component lower than the image signal; extracts a high-frequency image with a frequency component higher than the image signal; applies image quality enhancement processing to the low-frequency image; at least outputs the low-frequency image, whose image quality has been enhanced by the image quality enhancement processor, as an output image; and outputs, as the output image, an image signal including pixel values obtained by adding pixel values of individual pixels of the high-frequency image to pixel values of individual pixels of the low-frequency image, whose image quality has been enhanced, in accordance with condition information upon image capturing.

A program of an aspect of the present technology makes a computer function as: an endoscope provided with an objective lens at a tip of an insertion portion to be inserted into a body cavity; an image capturing unit that captures an optical image input from the endoscope and condensed by the objective lens, and that outputs the captured image as an image signal; a low-frequency component extracting unit that extracts a low-frequency image with a frequency component lower than the image signal; a high-frequency component extracting unit that extracts a high-frequency image with a frequency component higher than the image signal; an image quality enhancement processor that applies image quality enhancement processing to the low-frequency image; and an output unit that at least outputs the low-frequency image, whose image quality has been enhanced by the image quality enhancement processor, as an output image, and the output unit outputs, as the output image, an image signal including pixel values obtained by adding pixel values of individual pixels of the high-frequency image to pixel values of individual pixels of the low-frequency image, whose image quality has been enhanced, in accordance with condition information upon image capturing performed by the image capturing unit.

In an aspect of the present technology, an optical image is imaged that is input from an endoscope apparatus including an objective lens provided at a tip of a rigid insertion portion to be inserted into a body cavity and focused by the objective lens, to be output as an image signal; a low frequency image being a low frequency component is extracted from the image signal; a high frequency image being a high frequency component is extracted from the image signal; image quality improvement processing is performed to the low frequency image; and at least the low frequency image whose image quality is improved is output as an output image, and an image signal is output as the output image, including a pixel value in which a pixel value of each pixel of the high frequency image is added to a pixel value of each pixel of the low frequency image whose image quality is improved, depending on condition information at time of imaging.

Each of configurations of the endoscope system of an aspect of the present technology can be an independent apparatus, and can be a block for functioning as each of the configurations of the endoscope system.

Effects of the Invention

According to an aspect of the present technology, the conflicting effects can be adjusted to be well-balanced, such as the reduction of the processing load according to the image quality improvement processing of the image, and resolution improvement, depending on condition information according to the brightness at the time of imaging in the endoscope apparatus.

MODE FOR CARRYING OUT THE INVENTION

<Summary of Endoscope System>

Figure 1:
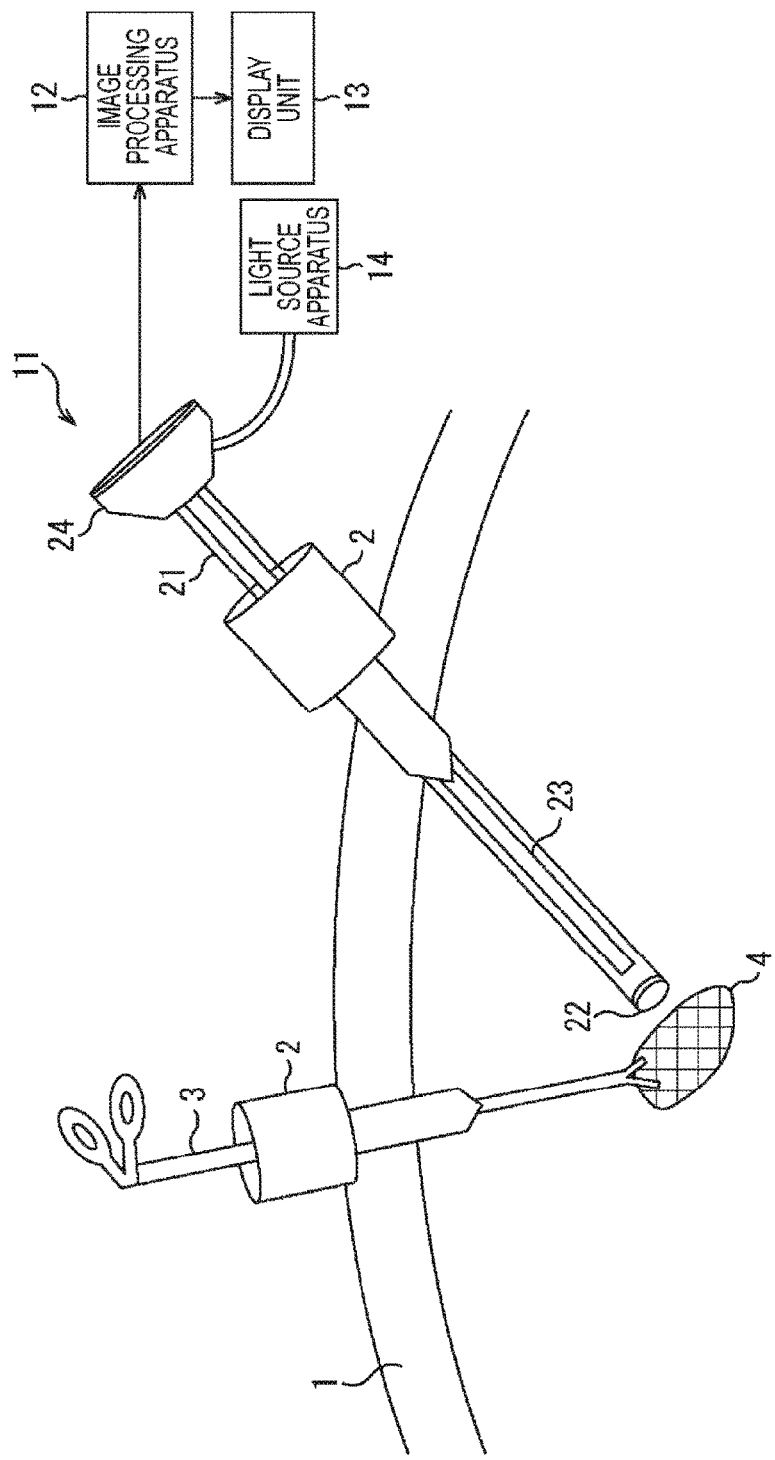
FIG. 1 is a diagram illustrating a summary of laparoscopic surgery.

FIG. 1 is a diagram for describing a summary of an endoscope system to which the present technology is applied.

The endoscope system is utilized in laparoscopic surgery that is performed instead of a conventional abdominal surgery in a medical site in recent years.

That is, as illustrated in FIG. 1, in the laparoscopic surgery, when an abdominal surgery is performed, for example, instead of laparotomizing by cutting an abdominal wall 1 that has conventionally been performed, an opening instrument called a trocar 2 is attached to the abdominal wall 1 in several places, and a laparoscope (hereinafter referred to as endoscope apparatus or endoscope) 11 and a treatment tool 3 are inserted into a body from a hole provided to the trocar 2. Then, while an image of an affected part (tumor and the like) 4 is viewed in real time that is video-imaged by the endoscope apparatus 11, treatment is performed such as ablation of the affected part 4 by the treatment tool 3.

In the linear rod-like endoscope apparatus 11 as illustrated in FIG. 1, a head part 24 is held by a surgeon, an assistant, an endoscope operator, a robot, or the like.

<Configuration Example of Endoscope System>

Figure 2:
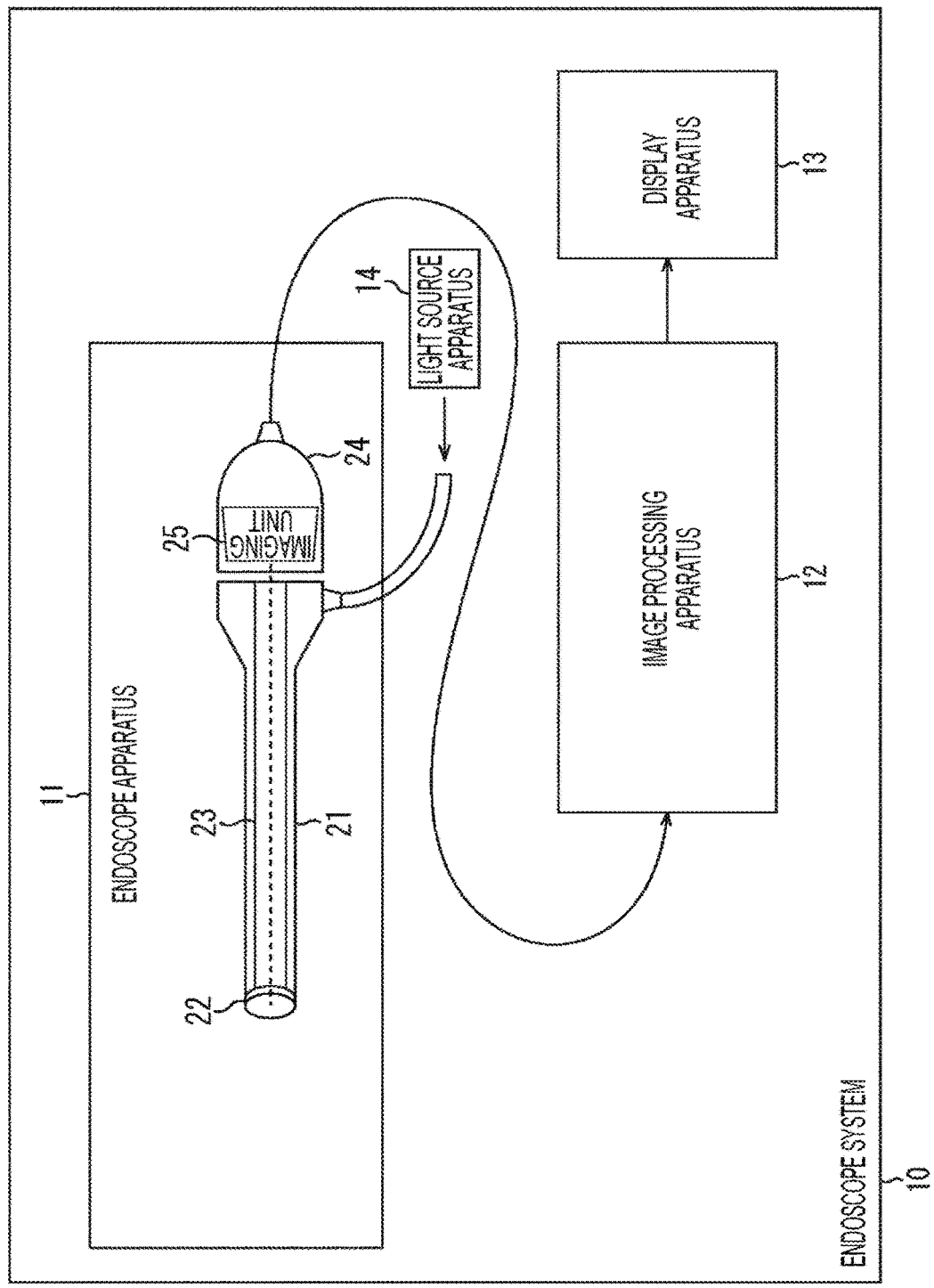
FIG. 2 is a block diagram illustrating a configuration example of an endoscope system to which the present technology is applied.

Here, referring to FIG. 2, a configuration example is described of an endoscope system being an embodiment of the present technology. An endoscope system 10 includes the endoscope apparatus 11, an image processing apparatus 12, and a display apparatus 13.

The endoscope apparatus 11 and the image processing apparatus 12 can be connected to each other wirelessly, in addition to being connected via a cable. In addition, the image processing apparatus 12 can be disposed in a place away from an operation room and can be connected via a network such as an in-house LAN and the Internet. It is the same for connection between the image processing apparatus 12 and the display apparatus 13.

The endoscope apparatus 11 includes a linear rod-like lens barrel part 21 and the head part 24. The lens barrel part 21 is referred to as a telescope or a rigid tube, and its length is about several tens of centimeters, and one end of a side to be inserted into the body is provided with an objective lens 22, and the other end is connected to the head part 24. An optical lens part 23 of a relay optical system is provided inside the lens barrel part 21. Incidentally, a shape of the lens barrel part 21 is not limited to a linear rod-like shape.

The lens barrel part 21, in rough classification, includes a direct viewing mirror in which its lens barrel axis and optical axis of FIG. 2 are equal, and an oblique viewing mirror in which its lens barrel axis and optical axis form a predetermined angle. The lens barrel part 21 of FIG. 2 is an example of the direct viewing mirror.

An imaging unit 25 is incorporated in the head part 24. The imaging unit 25 has an imaging element such as a Complementary Metal Oxide Semiconductor (CMOS) image sensor, and converts an optical image of the affected part that is input from the lens barrel part 21 into an image signal at a predetermined frame rate. In addition, the endoscope apparatus 11 is connected to a light source apparatus 14, and receives supply of a light source required for imaging to illuminate the affected part 4. At that time, the light source apparatus 14 is able to switch light of various wavelengths to emit, and is able to emit special light to identify particularly the affected part 4, in addition to normal light. Therefore, for the image that is imaged by the imaging unit 25, other than an image signal by the normal light, an image signal by the special light can also be imaged.

In the endoscope apparatus 11, the optical image of the affected part 4 focused by the objective lens 22 enters the imaging unit 25 of the head part 24 via the optical lens part 23, and is converted into the image signal of the predetermined frame rate by the imaging unit 25 to be output to the image processing apparatus 12 in a subsequent stage. In addition, the head part 24 has a configuration to provide to the image processing apparatus 12 information as condition information, such as a type of light emitted by the light source apparatus 14, an aperture of the objective lens 22, and an aperture of the optical lens part 23. The condition information, by providing a configuration for a user to input in advance to a portion not illustrated of the head part 24, can be provided to the image processing apparatus 12 as the condition information from the portion. In addition, it can be configured so that the image processing apparatus 12 recognizes by itself the condition information by analyzing the image signal that is imaged in the image processing apparatus 12. Here, description proceeds assuming that the condition information is input to the image processing apparatus 12 by any of the methods. Incidentally, it can be configured so that the information of the type of light that is provided to the image processing apparatus 12 from the light source apparatus 14 is provided directly to the image processing apparatus 12 from the light source apparatus 14.

Figure 3:
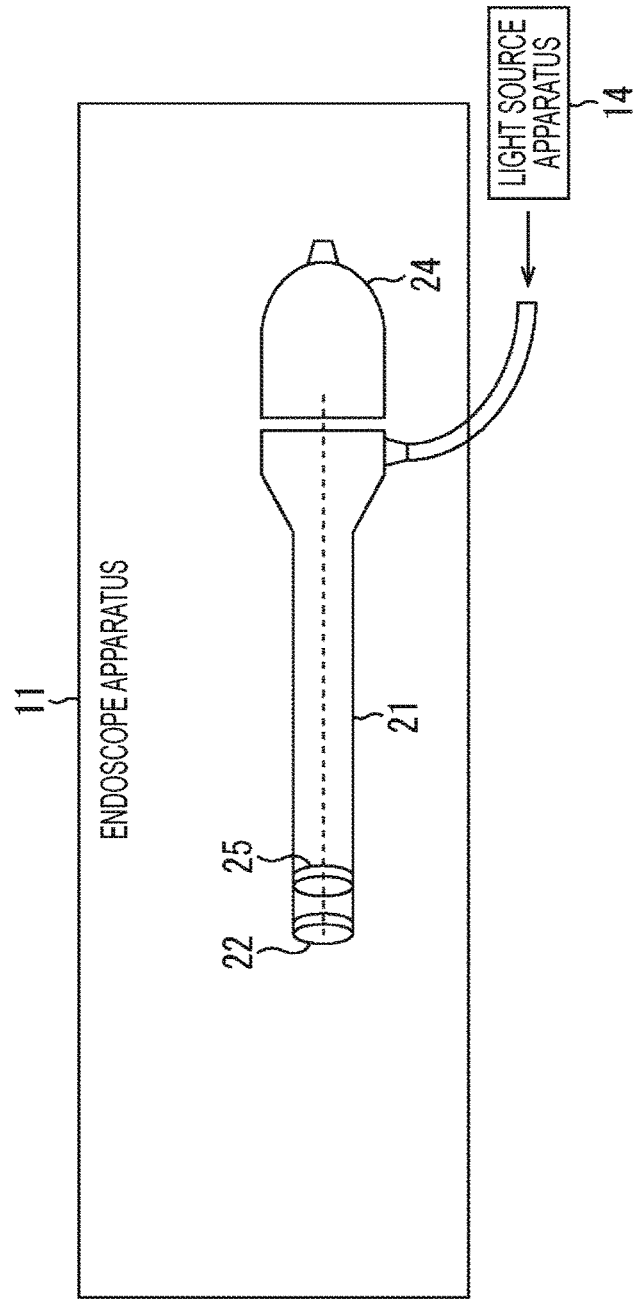
FIG. 3 is a block diagram illustrating another configuration example of the endoscope apparatus of FIG. 2.

FIG. 3 illustrates another configuration example of the endoscope apparatus 11. As illustrated in FIG. 3, the imaging unit 25 can be disposed immediately after the objective lens 22, and the optical lens part 23 inside the lens barrel part 21 can be omitted.

<First Embodiment of Image Processing Apparatus>

Figure 4:
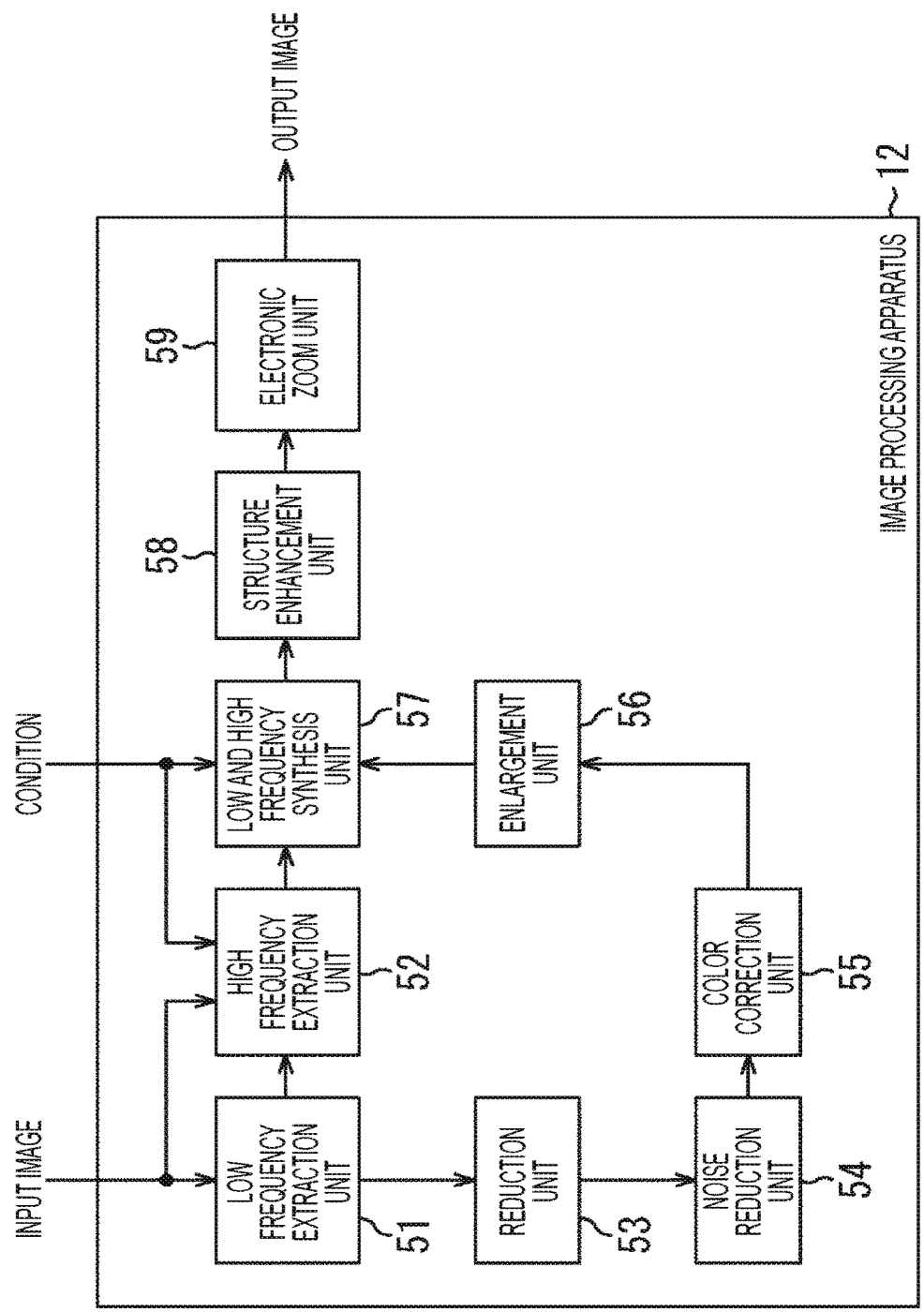
FIG. 4 is a diagram for describing a configuration example of a first embodiment of an image processing apparatus of FIG. 2.

Next, referring to a block diagram of FIG. 4, a configuration example is described of a first embodiment of the image processing apparatus 12.

The image processing apparatus 12 includes a low frequency extraction unit 51, a high frequency extraction unit 52, a reduction unit 53, a noise reduction unit 54, a color correction unit 55, an enlargement unit 56, a low and high frequency synthesis unit 57, a structure enhancement unit 58, and an electronic zoom unit 59.

The low frequency extraction unit 51 extracts a low frequency component in an input image to output the low frequency component to the high frequency extraction unit 52 and the reduction unit 53. In more details, the low frequency extraction unit 51 includes, for example, a Low Pass Filter (LPF), and extracts the low frequency component in the input image to output the low frequency component as the low frequency image to the high frequency extraction unit 52 and the reduction unit 53.

The high frequency extraction unit 52 extracts a high frequency component for each pixel of the input image to output the low frequency component to the low and high frequency synthesis unit 57. In more details, the high frequency extraction unit 52, for example, by subtracting the low frequency component to be provided from the low frequency extraction unit 51 for each pixel of the input image, extracts the high frequency component to be output to the low and high frequency synthesis unit 57. The high frequency extraction unit 52 stops extraction of the high frequency component when the high frequency component is unnecessary, depending on the condition information including a type of the light source emitted in the light source apparatus 14 and the apertures of the objective lens 22 and the optical lens part 23.

The reduction unit 53 reduces the image signal including the low frequency component into a low resolution image to output the image to the noise reduction unit 54 as a reduced image. In more details, the reduction unit 53 decreases pixel resolution to reduce a pixel signal of the image signal including the low frequency component by, for example, thinning at a predetermined interval.

The noise reduction unit 54 performs noise reduction processing of the reduced image. More specifically, the noise reduction unit 54, for example, performs 2Dimension Noise Reduction (2D NR) processing (Two-dimensional noise reduction processing) and 3Dimension Noise Reduction (3D NR) processing (Three-dimensional noise reduction processing) to the reduced image to reduce noise, and outputs the processed image to the enlargement unit 56. Here, the two-dimensional noise reduction processing is so-called spatial direction noise reduction processing using a signal in an image in the reduced image, and the three-dimensional noise reduction processing is so-called time direction noise reduction processing using a plurality of images in the time direction.

The color correction unit 55 performs color correction to the reduced image to which noise reduction processing is performed, to output the reduced image to the enlargement unit 56.

The enlargement unit 56 enlarges the reduced image to which band enhancement is performed by an enlargement ratio corresponding to a reduction ratio of when reduction processing is performed by the reduction unit 53, and converts the image to the same image size as the size of the input image, to output the image to the low and high frequency synthesis unit 57 as the low frequency image including the image signal of the low frequency component.

Figure 6:
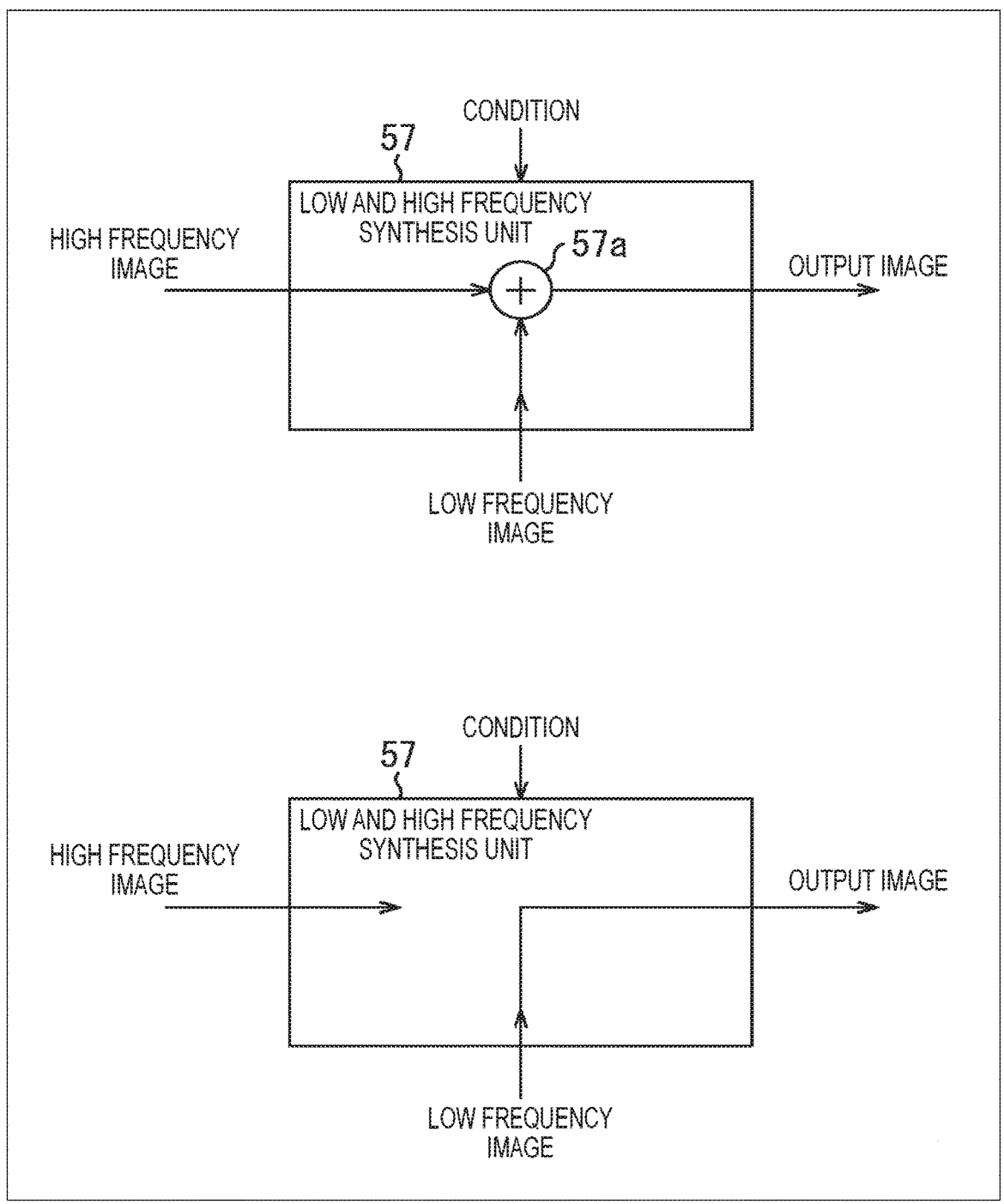
FIG. 6 is a diagram for describing operation of a low and high frequency synthesis unit.

The low and high frequency synthesis unit 57, based on the condition information that identifies brightness according to imaging such as a type of the light source from the light source apparatus 14, the optical lens part 23 in the endoscope apparatus 11, and an aperture size of the optical lens part 23, controls an addition unit 57*a* (FIG. 6) incorporated to output the image to the structure enhancement unit 58 as an image signal whose image quality is improved either of an image signal of only the low frequency component or an image signal in which the image signal of the high frequency component and the image signal of the low frequency component are added together.

That is, when any of the information is included as the condition information, such as information indicating that the light emitted by the light source apparatus 14 is the special light, information indicating that an aperture size of the objective lens 22 is smaller than a predetermined size, and information that the aperture size of the optical lens part 23 is smaller than a predetermined size, it results in that it is indicated that the brightness according to imaging is in a relatively dark state. In such a case, it results in that noise components are included a lot in the high frequency component particularly, in the input image. Therefore, for the case of such condition information, the low and high frequency synthesis unit 57 stops operation of the addition unit 57*a* (FIG. 6), and outputs the low frequency image including only the low frequency component whose image quality is improved, as an image quality improvement processing result. That is, in the case of special light imaging, from the fact that the noise components are included a lot in the high frequency component, by outputting only the low frequency image, it becomes possible to output an image being excellent in an S/N (signal to noise ratio) while being low resolution.

On the other hand, when all the information is included as the condition information such as information indicating that the light emitted by the light source apparatus 14 is the normal light including the white light, information that the aperture size of the objective lens 22 is larger than the predetermined size, and information that the aperture size of the optical lens part 23 is larger than the predetermined size, it results in that it is indicated that the brightness according to imaging is in a relatively bright state. In such a case, the noise component is relatively small even in the high frequency component. Therefore, the low and high frequency synthesis unit 57 controls the addition unit 57*a* (FIG. 6) to output a result in which the high frequency component is added to the low frequency component whose image quality is improved for each pixel, as the image quality improvement processing result. In this way, by switching the processing based on the condition information according to the brightness at time of imaging, an image whose image quality is improved appropriately is output to the subsequent stage in appropriate resolution. That is, in the case of normal light imaging, since the noise component is relatively small in the high frequency component, it becomes possible to output a high resolution and high quality image by adding a high frequency image to a low frequency image whose image quality is improved.

The structure enhancement unit 58 performs structure enhancement processing to the image signal whose image quality is improved to output the image signal to the electronic zoom unit 59.

The electronic zoom unit 59 electronically enlarges the image signal that is provided from the structure enhancement unit 58 and to which structure enhancement processing is performed, to an appropriate size for the display apparatus 13 to output the image signal.

<Image Processing by Image Processing Apparatus of FIG. 4>

Figure 5:
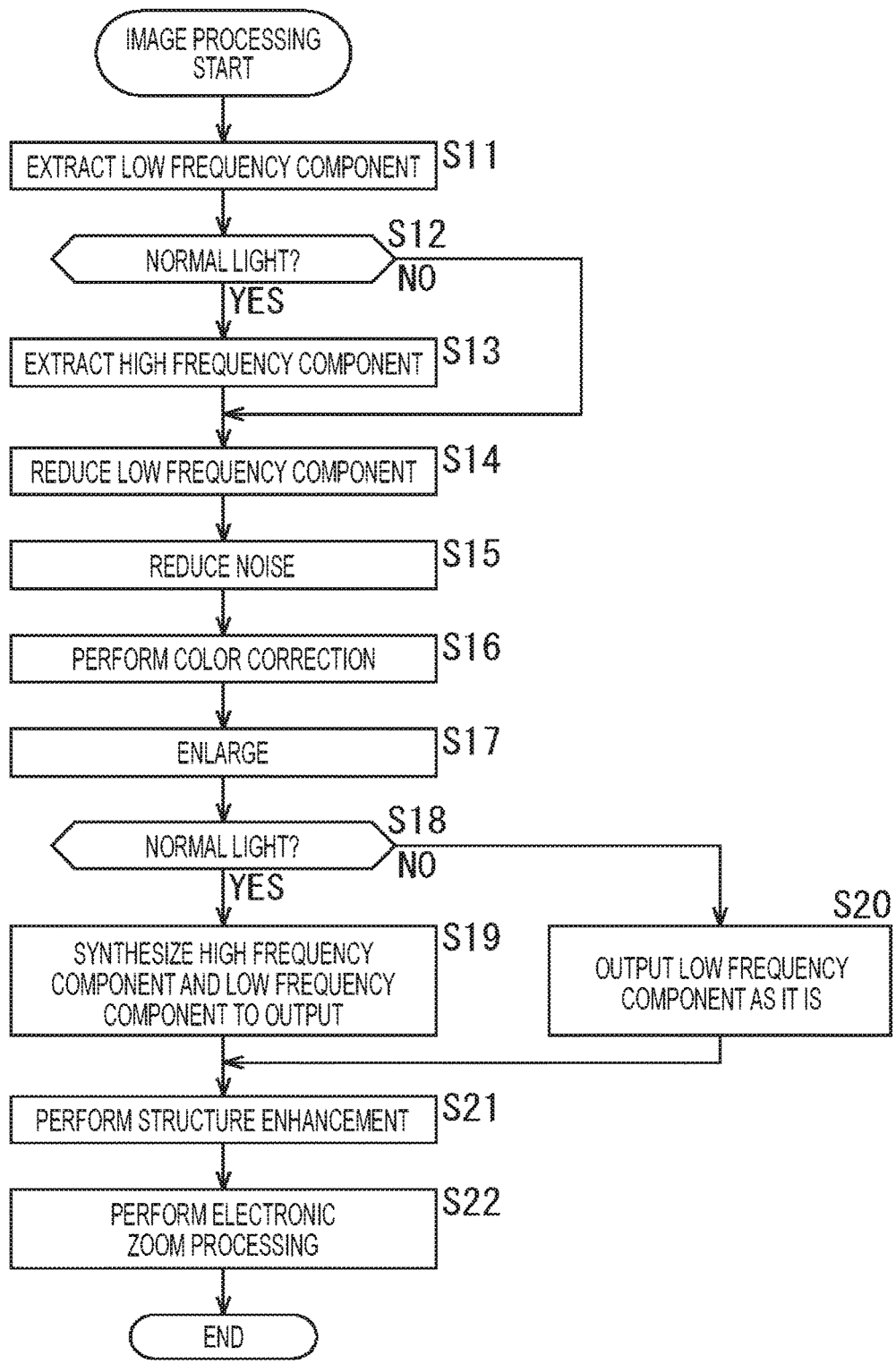
FIG. 5 is a flowchart for describing image processing by an image processing apparatus of FIG. 4.

Next, referring to a flowchart of FIG. 5, image processing by the image processing apparatus 12 of FIG. 4 is described. Incidentally, here, it is assumed that the condition information is provided indicating whether it is in a state of normal imaging emitting the white light being the normal light from the light source apparatus 14 to the image processing apparatus 12 or it is in a state of special light imaging emitting the special light. Further, it is assumed that the information of the objective lens 22 in the endoscope apparatus 11 and the information according to the aperture of the optical lens part 23 are also provided as the condition information to the image processing apparatus 12.

In step S11, the low frequency extraction unit 51 performs low frequency component extraction processing with the LPF for each pixel of the input image, and extracts the low frequency component to be output to the high frequency extraction unit 52 and the reduction unit 53.

In step S12, the high frequency extraction unit 52 determines whether or not the condition information from the light source apparatus 14 is condition information indicating the normal light imaging or an imaging state in the normal light that is relatively bright such as a case in which the objective lens 22 and the optical lens part 23 are used whose aperture is larger than the predetermined size. In step S12, for example, when the condition information is the one indicating that it is the imaging state in a relatively bright state, the processing proceeds to step S13.

In step S13, the high frequency extraction unit 52, by subtracting the low frequency component for each pixel of the input image, extracts the high frequency component and outputs the high frequency component to the low and high frequency synthesis unit 57. Incidentally, in step S12, when the condition information indicates the imaging state in a relatively dark state, the processing of step S13 is skipped. That is, in that case, as described later, the high frequency component is unnecessary in the subsequent stage, so that extraction is not performed of the image signal including the high frequency component. As a result, it becomes possible to reduce a processing load for extracting the high frequency component.

In step S14, the reduction unit 53 reduces the image size of the image signal including the low frequency component of the input image to output the image signal to the noise reduction unit 54, as the reduced image including the low frequency component.

In step S15, the noise reduction unit 54 performs noise reduction processing to the reduced image including the low frequency component to output the reduced image to the color correction unit 55.

In step S16, the color correction unit 55 performs color correction to the reduced image to which noise reduction processing is performed and that includes the low frequency component, to output the reduced image to the enlargement unit 56.

In step S17, the enlargement unit 56 enlarges the reduced image to which noise reduction is performed by an enlargement ratio corresponding to the reduction ratio of when reduction is performed in the reduction unit 53, and returns to the same image size as the input image to output the image to the low and high frequency synthesis unit 57.

In step S18, the low and high frequency synthesis unit 57, based on the condition information, determines whether or not it is the imaging state in the relatively bright state, and when it is indicated that it is the imaging state in the relatively bright state, the processing proceeds to step S19.

In step S19, the low and high frequency synthesis unit 57 adds the image signal (low frequency image) of the low frequency component that is provided from the enlargement unit 56 and to which noise reduction processing is performed and the image signal (high frequency image) of the high frequency component that is provided from the high frequency extraction unit 52 together to synthesize, and outputs the synthesized image signal to the structure enhancement unit 58 as the image (output image) whose image quality is improved. That is, the low and high frequency synthesis unit 57, as illustrated in the upper part of FIG. 6, controls the addition unit 57a in its inside to add the image signal (low frequency image) of the low frequency component that is provided from the enlargement unit 56 and to which noise reduction processing is performed and the image signal (high frequency image) of the high frequency component that is provided from the high frequency extraction unit 52 together. Then, the low and high frequency synthesis unit 57 outputs the image signal that is an addition result to the structure enhancement unit 58 at a high resolution and as the image signal (output image) whose image quality is improved.

On the other hand, in step S18, based on the condition information, when it is indicated that it is the imaging state in the relatively dark state, the processing proceeds to step S20.

In step S20, the low and high frequency synthesis unit 57 outputs only the image signal (low frequency image) including the low frequency component as it is that is provided from the enlargement unit 56 to the structure enhancement unit 58 as the image signal (output image) to which noise reduction processing is performed. That is, the low and high frequency synthesis unit 57, as illustrated in the lower part of FIG. 6, stops operation in the addition unit 57a incorporated, and outputs only the image signal (low frequency image) of the low frequency component that is provided from the enlargement unit 56 and to which noise reduction processing is performed to the structure enhancement unit 58 as the image signal (output image) whose image quality is improved.

In step S21, the structure enhancement unit 58 performs structure enhancement processing to the image signal that is provided from the low and high frequency synthesis unit 57 to output the image signal to the electronic zoom unit 59.

In step S22, the electronic zoom unit 59 performs conversion processing to the image signal to which the structure enhancement processing is performed into resolution that is suitable in the display apparatus 13, and outputs the converted image signal to the display apparatus 13 to display.

With the above processing, based on the condition information, in a case of imaging in the normal light including the white light or the normal imaging in which brightness is sufficient such as imaging in a condition including the objective lens 22 and the optical lens part 23 of large apertures (a case in which the diameter of the lens barrel part (optical scope) 21 is large, and thick), from the fact that a ratio of a noise signal is low in the high frequency component of the image signal that is imaged, the image in which the high frequency component and the low frequency component whose image quality is improved are added together is output as the image to which noise reduction processing is performed.

On the other hand, in a case of imaging in the special light or imaging in which brightness is insufficient such as in the optical lens part 23 of a small aperture (a case in which the diameter of the lens barrel part (optical scope) 21 is small, and thin), from the fact that the ratio of the noise signal is high in the high frequency component of the image signal, without adding the high frequency component to the low frequency component, the image as it is of the low frequency component whose image quality is improved is output as the output image.

Figure 7:
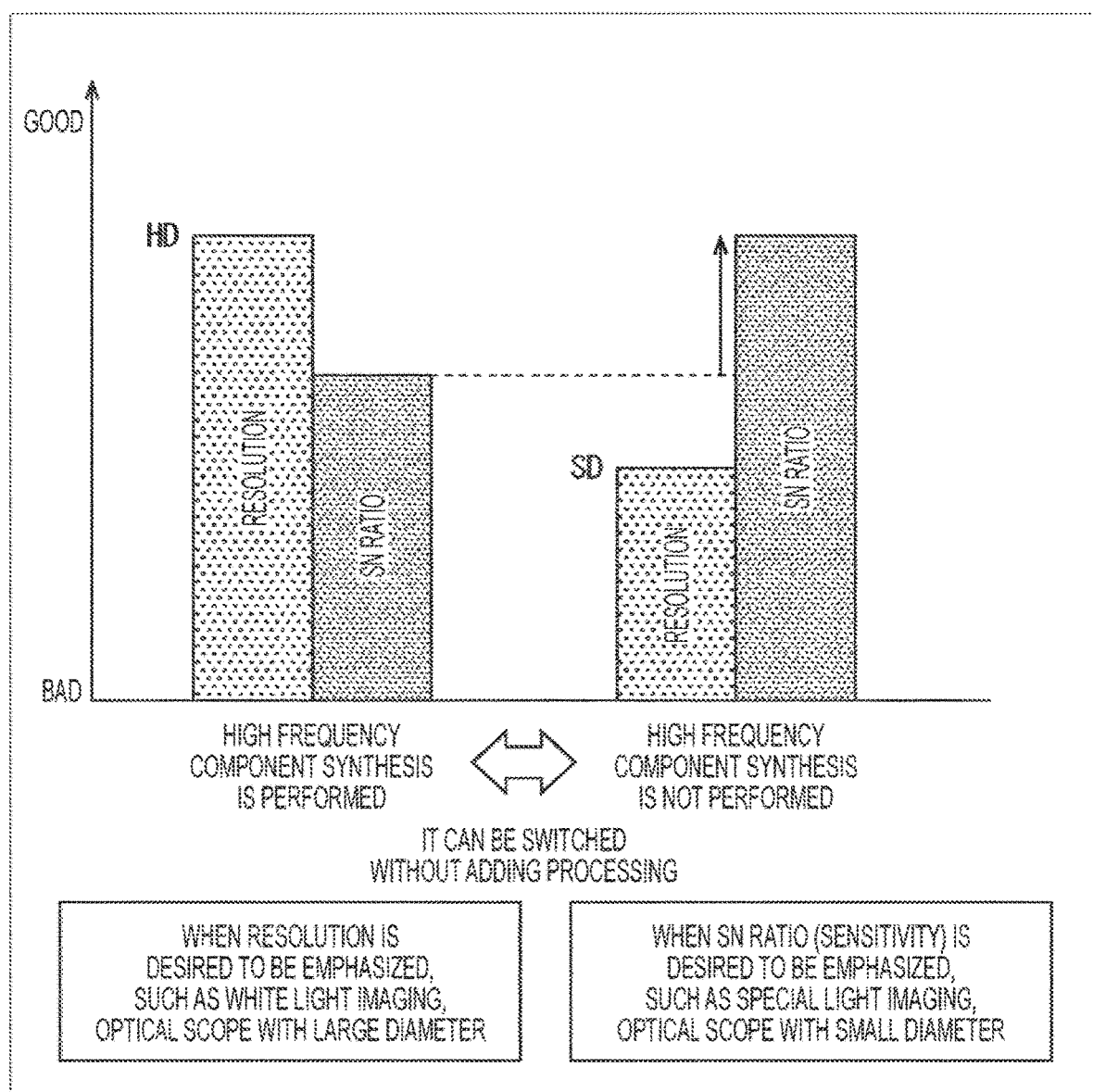
FIG. 7 is a diagram for describing an effect by image processing in the image processing apparatus of FIG. 2.

Thus, as illustrated in the left side of FIG. 7, in the white light imaging (normal imaging), since the noise component is small in the high frequency component, it becomes possible to output a high quality and high resolution image in contrast with the special light imaging illustrated in the right side in the figure. On the other hand, as illustrated in the right side in the figure, in the special light imaging, since the noise component is large in the high frequency component, it becomes possible to make the image be in a high S/N ratio state by the amount indicated by an arrow in the figure while being low resolution, in contrast with the white light imaging (normal imaging) illustrated in the right side in the figure.

Incidentally, in FIG. 7, in the left part, the resolution and the S/N ratio in the image to which the high frequency component is added are illustrated, and, in the right part, the resolution and the S/N ratio in the image to which the high frequency component is not added are illustrated.

Figure 8:
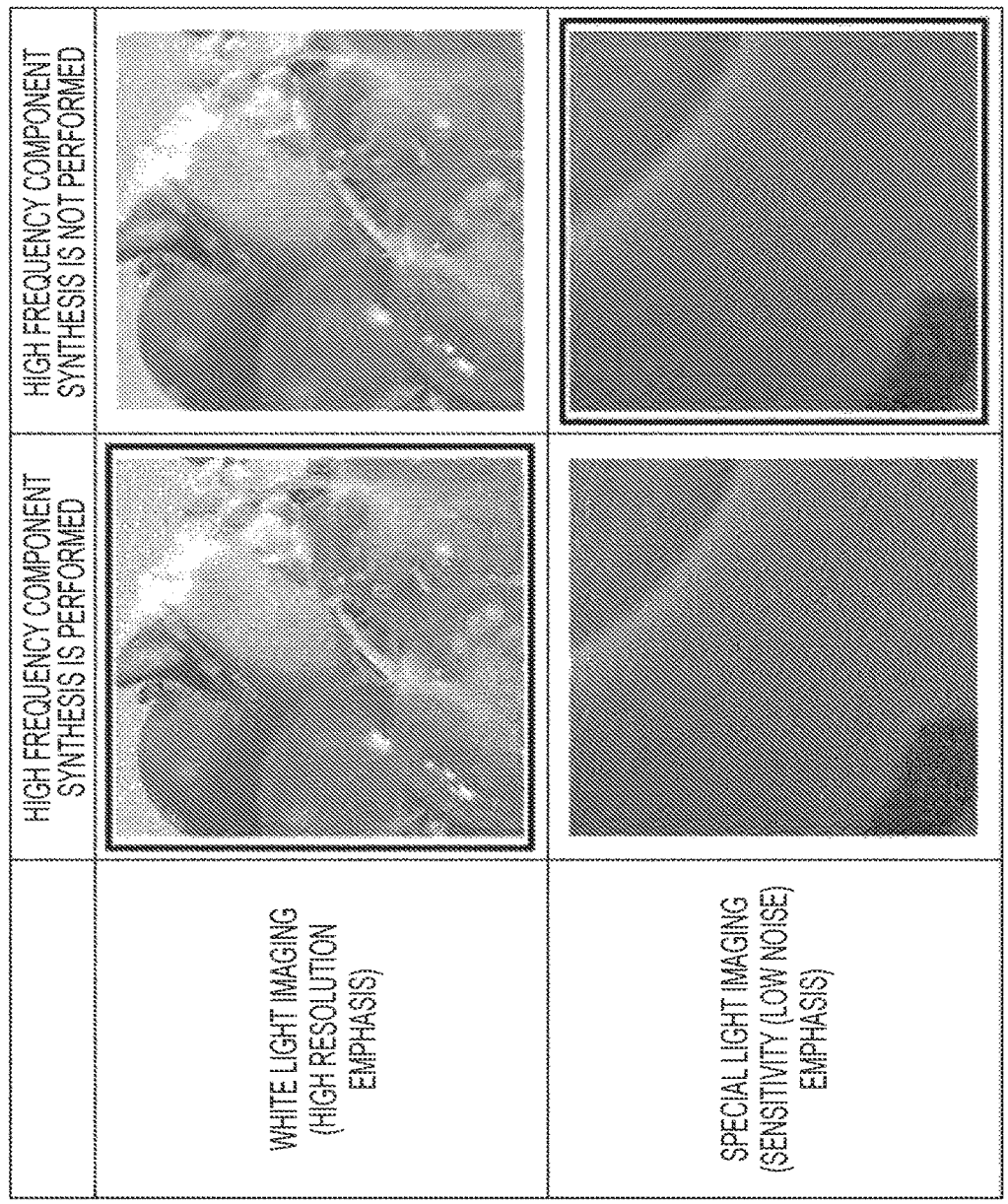
FIG. 8 is a diagram for describing an effect by the image processing in the image processing apparatus of FIG. 2.

That is, to the normal imaging in which the noise is small in the high frequency component, as illustrated in the image of the upper left part of FIG. 8, a higher resolution can be achieved than that of the image of the upper right part of FIG. 8, and a clearer image can be provided. In addition, to the special light imaging in which the noise is large in the high frequency component, as illustrated in the image of the lower right part of FIG. 8, by improving the S/N ratio better than the image of the lower left part of FIG. 8, it becomes possible to improve sensitivity, and to provide an image that is more easily recognized.

Incidentally, in FIG. 8, in the left part, the image is illustrated to which the high frequency component is added, and, in the right part, the image is illustrated to which the high frequency component is not added. Further, in FIG. 8, the images in the normal imaging are illustrated in the upper part, and the images in the special light imaging are illustrated in the lower part.

In addition, for the low frequency component, the image is reduced, and subjected to noise reduction and color correction, and then enlarged to be returned to the size of the input image, so that it becomes possible to reduce the processing load in each processing of the noise reduction and the color correction.

As a result, it becomes possible to display the image to which image quality improvement or improvement of the S/N ratio is performed appropriately depending on the imaging state.

In addition, in the above, the example has been described in which operation is stopped in the high frequency extraction unit 52 in the case of an imaging situation of a relatively dark environment in which the imaging condition includes the noise components a lot; however, in the low and high frequency synthesis unit 57, the high frequency component is not added to the low frequency component, so that it is possible to achieve the same effect even when the high frequency extraction unit 52 always operates.

<Second Embodiment of Image Processing Apparatus>

In the above, an example has been described in which a low frequency component of an input image is reduced to an image of a uniform size, and subjected to noise reduction and color correction, and then enlarged. However, a level of a ratio of a noise component included in a high frequency component, that is, an S/N ratio is reduced as it becomes dark, and the ratio of the noise is increased. Therefore, for example, a reduction size can be changed depending on an imaging condition such as the input image and brightness at time of imaging.

Figure 9:
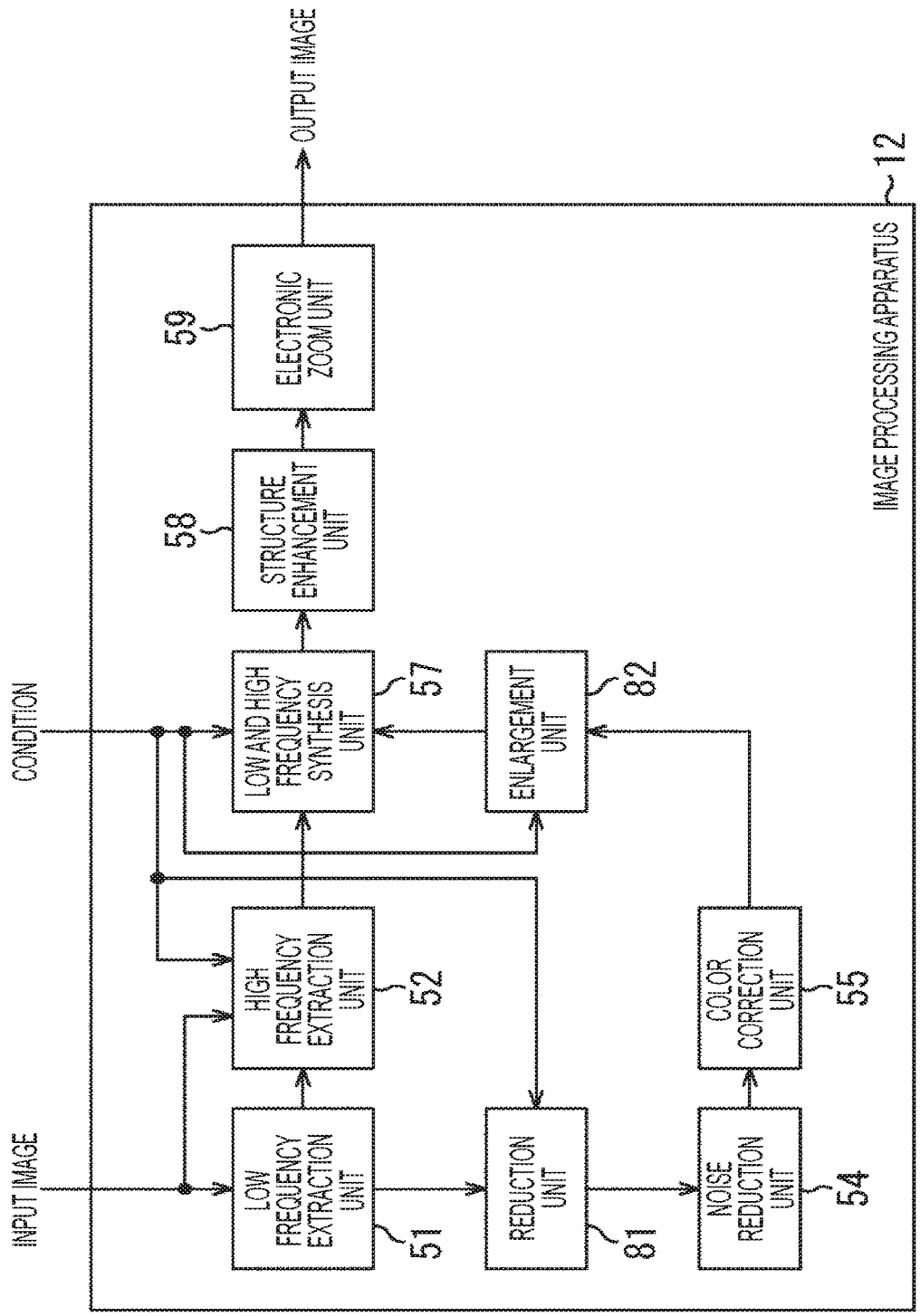
FIG. 9 is a diagram for describing a configuration example of a second embodiment of the image processing apparatus of FIG. 2.

FIG. 9 illustrates a configuration example of a second embodiment of an image processing apparatus 12 in which the reduction size is made to be changed depending on the imaging condition such as the input image and the brightness at the time of imaging. Incidentally, in the image processing apparatus 12 in FIG. 9, a difference from the image processing apparatus 12 in FIG. 4 is that a reduction unit 81 and an enlargement unit 82 are provided instead of the reduction unit 53 and the enlargement unit 56.

The reduction unit 81, although it is the same as the reduction unit 53 in a basic configuration, further, depending on the imaging condition, changes a reduction ratio and reduces the input image to output. That is, depending on the imaging condition, a higher reduction ratio is set for an image that is darker and whose noise component is large and S/N ratio is low, and the reduction ratio is made to be smaller as the condition is brighter and is closer to the normal imaging.

The enlargement unit 82, depending on the imaging condition, enlarges an image signal by an enlargement ratio corresponding to the reduction ratio of the reduction unit 81 to output the image signal to a low and high frequency synthesis unit 57.

That is, with such a configuration, since the image reduced by the reduction ratio depending on the imaging condition is subjected to the noise reduction and the color correction, and then enlarged to be output to the low and high frequency synthesis unit 57, it becomes possible to perform appropriate processing depending on a noise level of the input image, and it becomes possible to appropriately reduce a processing load.

<Image Processing in Image Processing Apparatus of FIG. 9>

Figure 10:
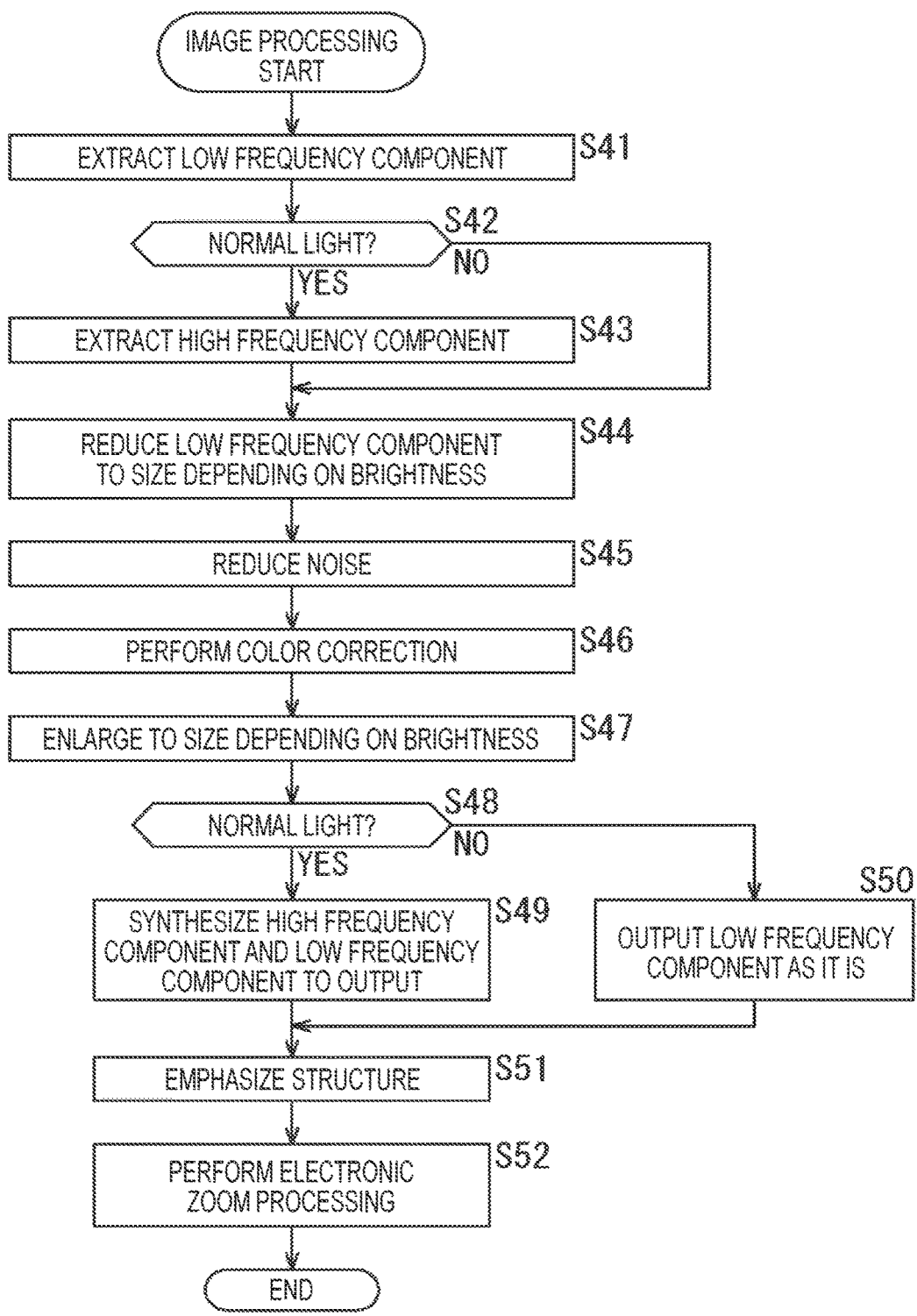
FIG. 10 is a flowchart for describing image processing by an image processing apparatus of FIG. 9.

Next, referring to a flowchart of FIG. 10, image processing in an image processing apparatus 12 of FIG. 9 is described. Incidentally, processing of steps S41-S43, S45, S46, S48-S52 in a flowchart of FIG. 10 is the same as the processing in steps S11-S13, S15, S16, S18-S22 in FIG. 5, so that descriptions thereof are omitted.

That is, in steps S41-S43 in FIG. 10, after image signals of the low frequency component and the high frequency component are extracted, in step S44, the reduction unit 81, based on condition information, makes the reduction ratio smaller and reduces to leave the size closer to the original image as the condition is closer to that of the normal imaging, and an image in which the high frequency component includes noise components a lot such as of special imaging is reduced to a smaller size.

When the noise reduction and the color correction are performed in steps S45, S46, in step S47, the enlargement unit 82, based on the condition information, enlarges the image by the enlargement ratio corresponding to the reduction ratio in the reduction unit 81 to output the image to the low and high frequency synthesis unit 57.

Then, in steps S48-S52, high and low frequency synthesis, structure enhancement, and electronic zoom processing are performed.

As a result, same as the processing described above, resolution and the S/N ratio are adjusted to be well-balanced depending on the imaging condition, and further, it becomes possible to appropriately reduce the processing load depending on the imaging condition.

<Example of Execution by Software>

By the way, a series of the processing described above can be executed by hardware; however, it can also be executed by software. When the series of the processing is executed by the software, a program configuring the software is installed from a recording medium to a computer incorporated in dedicated hardware, or, for example, a general purpose personal computer capable of executing various functions by installing various programs.

Figure 11:
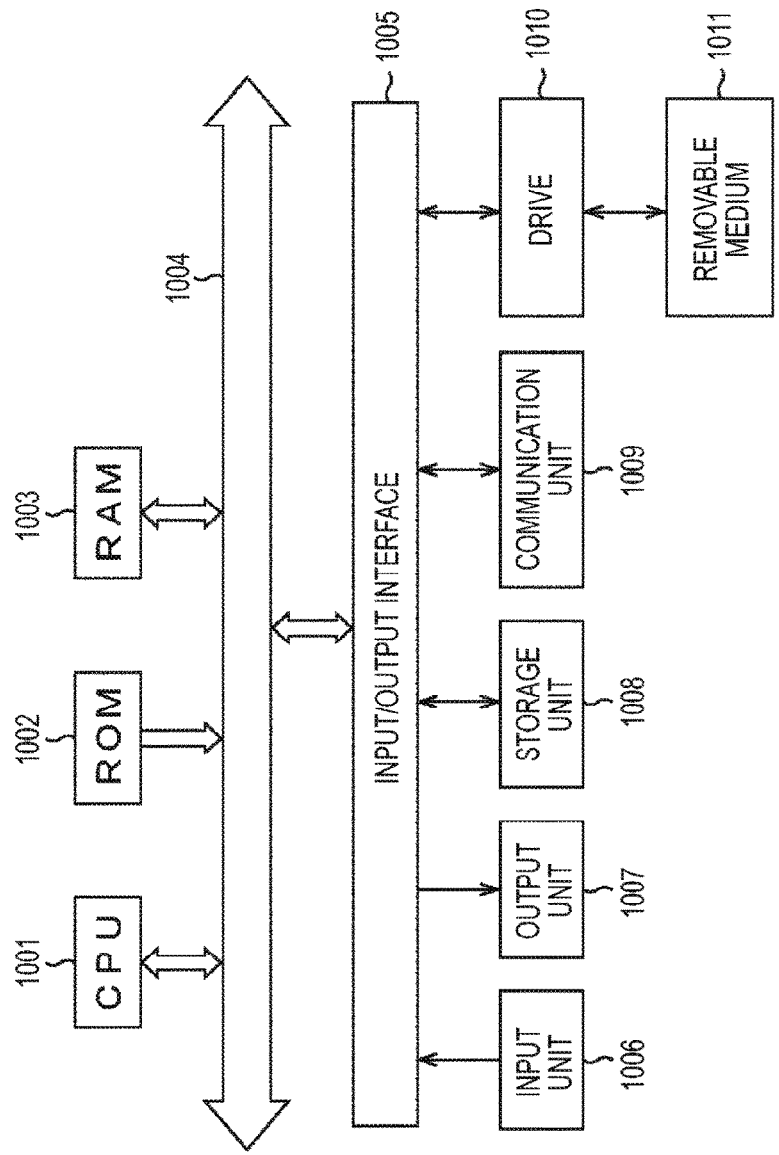
FIG. 11 is a diagram for describing a configuration example of a general purpose personal computer.

FIG. 11 illustrates a configuration example of the general purpose personal computer. The personal computer incorporates a Central Processing Unit (CPU) 1001. The CPU 1001 is connected to an input/output interface 1005 via a bus 1004. The bus 1004 is connected to Read Only Memory (ROM) 1002 and Random Access Memory (RAM) 1003.

The input/output interface 1005 is connected to an input unit 1006 including input devices such as a keyboard, a mouse for a user to input an operation command, an output unit 1007 for outputting to a display device a processing operation screen and an image of a processing result, a storage unit 1008 including a hard disk drive and the like for storing programs and various data, and a communication unit 1009 including a Local Area Network (LAN) adapter and the like for executing communication processing via a network typified by the Internet. In addition, a drive 1010 is connected for reading data from and writing data to a removable medium 1011 such as a magnetic disk (including flexible disk), an optical disk (including Compact Disc-Read Only Memory (CD-ROM), a Digital Versatile Disc (DVD)), a magneto optical disk (including Mini Disc (MD)), or a semiconductor memory.

The CPU 1001 executes various types of processing in accordance with a program stored in the ROM 1002, or a program read from the removable medium 1011, such as the magnetic disk, the optical disk, the magneto optical disk, or the semiconductor memory, to be installed to the storage unit 1008, and loaded to the RAM 1003 from the storage unit 1008. In the RAM 1003, data necessary for the CPU 1001 to execute the various types of processing is also stored appropriately.

In the computer configured as described above, for example, the CPU 1001 loads the program stored in the storage unit 1008 to the RAM 1003 via the input/output interface 1005 and the bus 1004 to execute the series of processing described above.

The program executed by the computer (CPU 1001) can be provided, for example, by being recorded in the removable medium 1011 as a package medium or the like. In addition, the program can be provided via a wired or wireless transmission medium such as a local area network, the Internet, digital satellite broadcasting.

In the computer, the program can be installed to the storage unit 1008 via the input/output interface 1005 by mounting the removable medium 1011 to the drive 1010. In addition, the program can be installed to the storage unit 1008 by receiving with the communication unit 1009 via the wired or wireless transmission medium. Further, the program can be installed in advance to the ROM 1002 and the storage unit 1008.

Incidentally, the program executed by the computer can be a program by which the processing is performed in time series along the order described herein, and can be a program by which the processing is performed in parallel or at necessary timing such as when a call is performed.

In addition, herein, a system means an aggregation of a plurality of constituents (apparatus, module (component), and the like), and it does not matter whether or not all of the constituents are in the same cabinet. Therefore, a plurality of apparatuses that is accommodated in a separate cabinet and connected to each other via a network and one apparatus that accommodates a plurality of modules in one cabinet are both systems.

Incidentally, the embodiment of the present technology is not limited to the embodiments described above, and various modifications are possible without departing from the scope of the present technology.

For example, the present technology can adopt a configuration of cloud computing that shares one function in a plurality of apparatuses via a network to process in cooperation.

In addition, each step described in the above flowchart can be executed by sharing in a plurality of apparatuses, other than being executed by one apparatus.

Further, when a plurality of pieces of processing is included in one step, the plurality of pieces of processing included in the one step can be executed by sharing in a plurality of apparatuses, other than being executed by one apparatus.

Incidentally, the present technology can also adopt the following configuration.

(1) An endoscope system including:

an endoscope apparatus including an objective lens provided at a tip of a rigid insertion portion to be inserted into a body cavity;

an imaging unit for imaging an optical image that is input from the endoscope apparatus and focused by the objective lens, to output the optical image as an image signal;

a low frequency component extraction unit for extracting a low frequency image being a low frequency component from the image signal;

a high frequency component extraction unit for extracting a high frequency image being a high frequency component from the image signal;

an image quality improvement processing unit for performing image quality improvement processing to the low frequency image; and an output unit for outputting as an output image at least the low frequency image whose image quality is improved by the image quality improvement processing unit, wherein the output unit outputs as the output image an image signal including a pixel value in which a pixel value of each pixel of the high frequency image is added to a pixel value of each pixel of the low frequency image whose image quality is improved, depending on condition information at time of imaging in the imaging unit.

(2) The endoscope system according to (1), wherein the condition information is information indicating whether or not it is a condition that increases a ratio of a noise component of the image signal that is imaged in the imaging unit.

(3) The endoscope system according to (2), wherein the information indicating whether or not it is the condition that increases the ratio of the noise component of the image signal that is imaged in the imaging unit, in the condition information, includes information indicating a type of light emitted by a light source apparatus for emitting illumination light when the imaging unit performs imaging, and information of an aperture of the objective lens in the endoscope apparatus and an aperture of a relay lens provided between the imaging unit and the objective lens.

(4) The endoscope system according to any one of (1) to (3), further including:

a reduction unit for reducing the low frequency image by a predetermined reduction ratio; and an enlargement unit for enlarging an image by an enlargement ratio corresponding to the reduction ratio, wherein the image quality improvement processing unit performs image quality improvement processing to the reduced low frequency image.

(5) The endoscope system according to (4), wherein:

the reduction unit reduces the low frequency image by a reduction ratio depending on the condition information; and the enlargement unit enlarges the reduced image of the low frequency image to which the image quality improvement processing has been performed, by a scaling ratio corresponding to the reduction ratio depending on the condition information.

(6) The endoscope system according to any one of (1) to (5), wherein the image quality improvement processing unit includes processing of spatial direction noise reduction, time direction noise reduction, color correction, and band enhancement.

(7) The endoscope system according to any one of (1) to (6), wherein the high frequency component extraction unit stops extraction of the high frequency image from the image signal when it is in the condition that increases the ratio of the noise component of the image signal that is imaged in the imaging unit, depending on the condition information at the time of imaging in the imaging unit.

(8) A method for operating an endoscope system including:

imaging an optical image that is input from an endoscope apparatus including an objective lens provided at a tip of a rigid insertion portion to be inserted into a body cavity and focused by the objective lens, to output the optical image as an image signal;

extracting a low frequency image being a low frequency component from the image signal;

extracting a high frequency image being a high frequency component from the image signal;

performing image quality improvement processing to the low frequency image;

outputting as an output image at least the low frequency image whose image quality is improved by the image quality improvement processing unit; and outputting as the output image an image signal including a pixel value in which a pixel value of each pixel of the high frequency image is added to a pixel value of each pixel of the low frequency image whose image quality is improved, depending on condition information at time of imaging.

(9) A program for causing a computer to function as:

an endoscope apparatus including an objective lens provided at a tip of a rigid insertion portion to be inserted into a body cavity;

an imaging unit for imaging an optical image that is input from the endoscope apparatus and focused by the objective lens, to output the optical image as an image signal;

a low frequency component extraction unit for extracting a low frequency image being a low frequency component from the image signal;

a high frequency component extraction unit for extracting a high frequency image being a high frequency component from the image signal;

an image quality improvement processing unit for performing image quality improvement processing to the low frequency image; and an output unit for outputting as an output image at least the low frequency image whose image quality is improved by the image quality improvement processing unit, wherein the output unit outputs as the output image an image signal including a pixel value in which a pixel value of each pixel of the high frequency image is added to a pixel value of each pixel of the low frequency image whose image quality is improved, depending on condition information at time of imaging in the imaging unit.

REFERENCE SIGNS LIST

2 Trocar
10 Endoscope system
11 Endoscope apparatus
12 Image processing apparatus
13 Display apparatus
14 Light source apparatus
21 Lens barrel part
22 Objective lens
23 Optical lens part
24 Head part
25 Imaging unit
51 Low frequency extraction unit
52 High frequency extraction unit
53 Reduction unit
54 Noise reduction unit
55 Color correction unit
56 Enlargement unit
57 Low and high frequency synthesis unit
58 Structure enhancement unit
59 Electronic zoom
81 Reduction unit
82 Enlargement unit

The invention claimed is:

1. A medical image processing system comprising:
a medical imaging device that captures an optical image and that outputs the captured optical image as an image signal;
a low-frequency image generation processor that generates a low-frequency image corresponding to low-frequency components of the image signal;
a high-frequency image generation processor that generates a high-frequency image corresponding to high-frequency components of the image signal;
an image quality enhancement processor that applies image quality enhancement processing to the low-frequency image; and
output circuitry that selectively outputs (a) the enhanced low-frequency image, whose image quality has been enhanced by the image quality enhancement processor, as an output image, or (b) an output image, which has a 4K or more resolution and is obtained by adding the high-frequency image to the enhanced low-frequency image, based on condition information of the medical imaging device.

2. The medical image processing system according to claim 1, further comprising:
a size-reduction processor that reduces a size of the low-frequency image at a specified scaling ratio; and
an enlargement processor that enlarges an image at the specified scaling ratio,
wherein the image quality enhancement processor applies image quality enhancement processing to the size-reduced low-frequency image.

3. The medical image processing system according to claim 1,
wherein the image quality enhancement processor includes processing of spatial-directional noise reduction, time-directional noise reduction, color correction, and frequency band emphasis.

4. The medical image processing system according to claim 1,
wherein the high-frequency image generation processor stops extracting the high-frequency image from the image signal when a condition is satisfied, under which the image signal captured by the medical imaging device has a higher proportion of a noise component, in accordance with the condition information upon the capturing of the optical image performed by the medical imaging device.

5. The medical image processing system according to claim 1, wherein the medical imaging device includes an endoscope with an objective lens at a tip of an insertion portion of the endoscope to be inserted into a body cavity and an image sensor that captures the optical image.

6. The medical image processing system according to claim 1, wherein the condition information is information indicating modes of illuminating light or of the medical imaging device.

7. The medical image processing system according to claim 6, wherein the modes include a normal imaging mode using white light illumination, or a special imaging mode using special light illumination.

8. The medical image processing system according to claim 7, wherein the output circuitry outputs the enhanced low-frequency image when the condition information indicates the special imaging mode using the special light illumination.

9. The medical image processing system according to claim 7, wherein the output circuitry outputs the output image obtained by adding the high-frequency image to the enhanced low-frequency image when the condition information indicates the normal imaging mode using the white light illumination.

10. The medical image processing system according to claim 7, wherein the special imaging mode is a mode of illuminating using one of an infrared illumination light or a narrow wavelength band illumination.

11. The medical image processing system according to claim 1, wherein the condition information is information indicating a quality requirement of the output image.

12. The medical image processing system according to claim 11, wherein the quality requirement is a requirement of spatial resolution or a requirement of signal/noise ratio.

13. An operation method of a medical image processing system, the method comprising:
with a medical imaging device, capturing an optical image and outputting the captured optical image as an image signal;

generating, with a low-frequency image generation processor, a low-frequency image corresponding to low-frequency components of the image signal;

generating, with a high-frequency image generation processor, a high-frequency image corresponding to high-frequency components of the image signal;

applying, with an image quality enhancement processor, image quality enhancement processing to the low-frequency image; and selectively outputting, with output circuitry, (a) the enhanced low-frequency image, whose image quality has been enhanced by the image quality enhancement processor, as an output image, or (b) an output image, which has a 4K or more resolution and is obtained by adding the high-frequency image to the enhanced low-frequency image, based on condition information of the medical imaging device.

14. A non-transitory computer-readable storage medium including computer-program instructions which, when executed by a computer, cause the computer to perform a method of operating a medical image processing system, the method comprising:

with a medical imaging device, capturing an optical image and outputting the captured optical image as an image signal;

generating, with a low-frequency image generation processor, a low-frequency image corresponding to low-frequency components of the image signal;

generating, with a high-frequency image generation processor, a high-frequency image corresponding to high-frequency components of the image signal;

applying, with an image quality enhancement processor, image quality enhancement processing to the low-frequency image; and selectively outputting, with output circuitry, (a) the enhanced low-frequency image, whose image quality has been enhanced by the image quality enhancement processor, as an output image, or (b) an output image, which has a 4K or more resolution and is obtained by adding the high-frequency image to the enhanced low-frequency image, based on condition information of the imaging device.

15. A medical image processing apparatus comprising:

a low-frequency image generating processor that extracts a low-frequency image corresponding to low-frequency components of an image signal of an optical image;

a high-frequency image generating processor that extracts a high-frequency image corresponding to high-frequency components of the image signal;

an image quality enhancement processor that applies image quality enhancement processing to the low-frequency image; and output circuitry that selectively outputs, as an output image, (a) the enhanced low-frequency image, whose image quality has been enhanced by the image quality enhancement processor, or (b) an image, which has a 4K or more resolution and is obtained by adding the high-frequency image to the enhanced low-frequency image, based on condition information of an imaging device that captured the optical image.

* * * * *